United States Patent
Fereira et al.

(10) Patent No.: US 7,074,423 B2
(45) Date of Patent: Jul. 11, 2006

(54) OSMOTIC DELIVERY SYSTEM WITH EARLY ZERO ORDER PUSH POWER ENGINE

(75) Inventors: Pamela J. Fereira, Santa Clara, CA (US); Stephen A. Berry, Hollister, CA (US)

(73) Assignee: Alza Corporation, Palo Alto, CA (US)

( * ) Notice: Subject to any disclaimer, the term of this patent is extended or adjusted under 35 U.S.C. 154(b) by 270 days.

(21) Appl. No.: 10/463,300

(22) Filed: Jun. 17, 2003

(65) Prior Publication Data
US 2004/0097906 A1 May 20, 2004

(51) Int. Cl.
*A61F 2/00* (2006.01)

(52) U.S. Cl. .................................. 424/423

(58) Field of Classification Search ........ 604/890.1, 604/892.1; 424/422–425
See application file for complete search history.

(56) References Cited

U.S. PATENT DOCUMENTS

| | | |
|---|---|---|
| 4,034,756 A | 7/1977 | Higuchi et al. |
| 4,609,374 A | 9/1986 | Ayer |
| 4,783,337 A | 11/1988 | Wong et al. |
| 4,874,388 A | 10/1989 | Wong et al. |
| 5,023,088 A | 6/1991 | Wong et al. |
| 5,209,746 A | 5/1993 | Balaban et al. |
| 5,368,863 A | 11/1994 | Eckenhoff et al. |
| 5,413,572 A | 5/1995 | Wong et al. |
| 5,595,759 A | 1/1997 | Wright et al. |
| 5,728,396 A | 3/1998 | Peery et al. |
| 5,795,591 A | 8/1998 | Lee et al. |
| 5,938,654 A | 8/1999 | Wong et al. |
| 5,985,305 A | 11/1999 | Peery et al. |
| 5,997,902 A | 12/1999 | Maruyama et al. |
| 6,132,420 A | 10/2000 | Dionne et al. |

FOREIGN PATENT DOCUMENTS

WO    WO 98/20930    5/1998

OTHER PUBLICATIONS

PCT International Search Report, dated Sep. 2, 2003, 3 pages.

*Primary Examiner*—Sharon Kennedy
(74) *Attorney, Agent, or Firm*—TraskBritt

(57) ABSTRACT

The present invention is directed to an osmotic engine useful in an osmotic delivery system for delivery of a beneficial agent in a controlled manner over a preselected administration period. By including a flowable engine comprising at least one osmotic agent and at least one fluid vehicle, the resulting osmotic engine reaches a zero order push power or push rate quickly and provides steady delivery of the beneficial agent.

19 Claims, 3 Drawing Sheets

OSMOTIC DELIVERY SYSTEM WITH EARLY ZERO ORDER PUSH POWER ENGINE

FIELD OF THE INVENTION

This present invention is directed to an osmotic engine useful in an osmotic delivery system for delivery of a beneficial agent in a controlled manner over a preselected administration period, to osmotic delivery systems containing the osmotic engine, and to methods for preparing both the osmotic engine and the osmotic delivery system.

BACKGROUND OF THE INVENTION

It has been a goal in the drug delivery field to treat a disease by prolonged delivery of a beneficial agent, such as a drug, at a controlled rate. Various approaches have been taken toward this end. For example, implantable diffusional systems have been used to deliver a drug that is released by simple diffusion. In another approach, osmotic delivery systems have been used to provide more accurately controlled delivery than simple diffusion. The osmotic delivery systems can be implanted into a living organism to release the beneficial agent in a controlled manner over a preselected administration period.

In general, implantable osmotic delivery systems operate by imbibing fluid from the outside environment and releasing a corresponding amount of the beneficial agent. An implantable osmotic delivery system typically contains as part of its wall a semipermeable membrane that allows fluid to pass through from the external environment but not particles. The semipermeable membrane is next to a compartment containing an osmotic agent that is capable of imbibing water. When the system is placed in a fluid environment, water is imbibed from the environment into the system by the osmotic agent, resulting in expansion of the osmotic agent. The expanded osmotic agent generates a pressure on the beneficial agent, which is located directly next to the osmotic agent or on the other side of a movable partition or piston from the osmotic agent, and forces the beneficial agent to pass through an opening to the outside environment. Various osmotic delivery systems have been described in, for example, U.S. Pat. Nos. 6,132,420; 5,985,305; 5,938,654; 5,795,591; 5,728,396; 5,595,759; 5,413,572; 5,368,863; 4,783,337; and 4,609,374, which are incorporated by reference herein in their entirety.

Most current implantable osmotic delivery systems comprise a semipermeable membrane that is in liquid communication with an osmotic agent or engine compartment, a movable partition or piston separating the engine compartment from the beneficial agent compartment or reservoir, and an orifice or exit that is in communication with both the beneficial agent in the reservoir and the exterior of the osmotic delivery system.

Beneficial agent delivery from implantable osmotic delivery systems can be accomplished in a variety of ways. The beneficial agent can be delivered in a controlled manner that is dependent upon the push power profile of the osmotic engine. The beneficial agent delivery rate can also be varied. For example, the flow of beneficial agent from the system can be partially retarded by placing an elastic membrane or band over the exit (for example, U.S. Pat. No. 5,209,746, which is incorporated by reference herein in its entirety). The elastic membrane or band stretches with an increase of pressure in the system until the internal pressure causes the membrane to separate sufficiently from the orifice to permit escape of the beneficial agent (this type of delivery can be termed pulsatile delivery).

Most current implantable osmotic delivery systems contain engines that comprise dry tablets comprising the osmotic agent. Due to machining and tableting tolerances, the osmotic tablet is generally slightly smaller than the compartment in which the tablet is placed. A filler can be used to fill the gap between the tablet and the compartment wall (for example, U.S. Pat. No. 6,132,420 which is incorporated by reference herein in its entirety). However, there are potential disadvantages to this kind of engine.

For instance, an osmotic delivery system that includes an osmotic engine comprising a tableted osmotic composition may require a startup time that is undesirably long. As it is used herein, the term "startup time" refers to the time from introduction of the osmotic system into the environment of use until the active agent is actually delivered from the osmotic system at a rate not less than approximately 70% of the intended steady-state rate (See, for example, U.S. Pat. No. 5,985,305, which is incorporated by reference herein in its entirety). The time required for the intended steady-state delivery rate is dependent upon a number of factors. For instance, the semipermeable membrane must be wet and fluid must flow through the semipermeable membrane into the osmotic engine compartment. After passing through the semipermeable membrane, fluid must also wet the osmotic tablets sufficiently to cause them to swell. The swelling of the osmotic tablet material then moves the movable partition or piston between the osmotic tablet and the beneficial agent toward the exit or orifice. This movement of the movable partition or piston toward the exit or orifice pushes the beneficial agent to and through the exit or orifice. Due to the manner in which tableted osmotic engines are manufactured, the time required to achieve movement of the movable partition or piston such that startup is achieved may constitute a significant portion of the anticipated life of the osmotic delivery system.

In particular, during the manufacture of tableted osmotic engines or during the loading of osmotic engine tablets into the engine compartment of an osmotic delivery system, air is typically entrapped within the tableted composition, between the filler and the engine tablet, between the filler and a wall of the osmotic delivery system, or inside the filler itself, particularly where a dry filler material is used. The compressibility of the tableted composition results in a delay in startup as the entrapped air is compressed and causes the osmotic engine to expand at a rate that is less than proportional to the volume of water imbibed through the semipermeable membrane, at least until startup is achieved. If too much air is entrapped during the manufacture of the tableted osmotic engine or during assembly of the osmotic delivery system, the startup time of the system may be undesirably high for a desired application. Moreover, the amount of air entrapped may vary from one system to another, resulting in startup performance that varies significantly from system to system.

Another potential disadvantage of an osmotic delivery device that includes an osmotic engine formed using a tableted osmotic composition is that such an osmotic engine requires at least one manufacturing step that may be avoided. In a presently available system (DUROS® system, ALZA Corporation, Mountain View, Calif.), the osmotic engine contains both the tableted osmotic composition and a filler composition, which serves to reduce or minimize entrapped air within the engine compartment. To manufacture such an engine, the engine filler (or compound used to fill in gaps around the tablets) is loaded into the engine compartment first. After the filler is loaded, one or more osmotic tablets are positioned within the same compartment such that the filler flows around the tablets. In some instances, excess filler may overflow the engine compartment. Where such is the case, it may not be certain how much filler is left in each engine and the ratio of osmotic agent to filler may vary among engines. However, if the osmotic material included in the engine itself worked to minimize or reduce entrapped compressible gas within the compartment, the step of loading the filler into the engine compartment and the uncertainties that such a step may introduce could be eliminated. Therefore, it would be an improvement in the art to provide an osmotic delivery system that includes an osmotic engine that is easily manufactured, works to reduce or minimize entrapped air, and possesses a more predictable composition from system to system.

SUMMARY OF THE INVENTION

The present invention relates to an osmotic engine that reaches zero order push power relatively quickly after being placed in a fluid environment of use. The present invention also relates to the manufacture of osmotic engines with rapid achievement of zero order push power and to the manufacture of osmotic delivery systems containing such engines. The present invention also relates to an osmotic delivery system whose osmotic engine reaches zero order push power soon after being placed in a fluid environment of use. In other words, the startup time for a three-month delivery system is less than 10% of the anticipated life of the osmotic delivery system. This startup time is achieved by including in the system an osmotic engine that comprises a viscous, flowable composition. The osmotic agent composition is preferably prepared by mixing an osmotic agent and a fluid vehicle to result in a viscous, flowable composition in which the osmotic agent is evenly distributed. The preferred osmotic agent composition can then be loaded into the osmotic delivery system in a one-step process. Since the composition is flowable rather than dry, less air is entrapped. Furthermore, the flowable composition may be de-aerated prior to being loaded into the system in order to remove any residual entrapped air. As a result, the osmotic engine starts up quickly and reaches a zero order push rate early, and engine performance is much less variable from system to system.

The osmotic engine of the present invention can have a vehicle with some osmotic power but the engine composition must rapidly achieve zero order push power. The amount or intensity of the push power needed for the engine composition depends on the beneficial agent composition to be delivered. For example, if the beneficial agent composition is a liquid, less engine push power is required to deliver the beneficial agent than if the beneficial agent composition is a very viscous composition. Thus, the osmotic engine composition is chosen to provide sufficient zero order push power to deliver the beneficial agent composition for the anticipated delivery time.

Accordingly, one aspect of the present invention provides a flowable osmotic engine useful in an implantable osmotic system for delivering a beneficial agent to a fluid environment of use, the engine comprising:
  (a) at least one osmotic agent; and
  (b) a fluid vehicle with limited osmotic power;
wherein the osmotic agent and the vehicle form a viscous, flowable composition that increases in size upon imbibing fluid from the fluid environment through a semipermeable membrane in the osmotic system.

Also provided in the present invention is an osmotic system for delivering a beneficial agent to a fluid environment of use, comprising:
  (a) a wall comprising in part a semipermeable membrane which allows fluid to pass through the membrane from the fluid environment;
  (b) a reservoir containing the beneficial agent, the reservoir being inside the wall and having an exit passageway connecting the exterior fluid environment with the interior of the reservoir; and
  (c) a viscous osmotic engine inside the wall and in contact with the semipermeable membrane, the engine comprising a viscous, flowable composition of at least one osmotic agent suspended in a fluid vehicle, the vehicle having limited osmotic power; wherein the engine increases in size upon imbibing fluid from the fluid environment through the semipermeable membrane, and the increase in size forces the beneficial agent composition to pass through the passageway outward to the fluid environment of use.

Another aspect of the present invention provides a method for delivering a beneficial agent into a fluid environment of use, comprising:
  (a) placing an osmotic system in the fluid environment of use, the osmotic system comprising a viscous osmotic engine, the engine being a flowable composition prepared by suspending at least one osmotic agent in a fluid vehicle with limited osmotic power; and
  (b) allowing the osmotic engine to imbibe fluid from the fluid environment through a semipermeable membrane and expand so as to force the beneficial agent into the fluid environment.

DETAILED DESCRIPTION OF THE INVENTION

Figure 1:
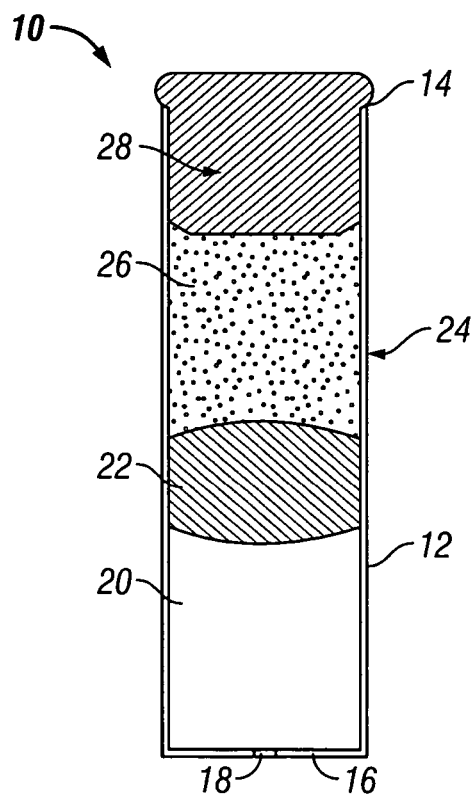
FIG. 1 is a schematic diagram of an exemplary osmotic system according to the present invention.

In the present invention, the osmotic agent and the fluid vehicle are mixed to form a flowable composition in which the osmotic agent is homogenously suspended in the fluid vehicle prior to being loaded into the engine compartment. The advantages of this flowable engine are several fold. The two-step assembly process becomes one, and the process of tableting is eliminated. Furthermore, the flowable engine composition contains less entrapped air than a dry tablet, and the flowable composition can be further de-aerated to remove the remaining entrapped air. Without entrapped air, the engine can expand at a regular rate more quickly and the startup time is reduced. Moreover, since the osmotic agent is evenly distributed in the flowable engine, the engine imbibes fluid at a more constant rate. These effects, coupled with the fact that the ratio of osmotic agent to fluid vehicle is now the same among engines, reduce the variation from one engine to another.

Definitions

The terms used in this application are defined as follows unless otherwise indicated:

The term "air" simply refers to any compressible gas present in the environment where an osmotic engine or osmotic delivery system is manufactured.

An "osmotic agent" is a material that is capable of expanding in size upon imbibing water. As used herein, the osmotic agent may be an osmagent, an osmopolymer, or a mixture of the two. Species that fall within the category of osmagent, i.e., the nonvolatile species that are soluble in water and create the osmotic gradient driving the osmotic inflow of water, vary widely. Examples are known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species that fall within the category of osmopolymer are hydrophilic polymers that swell upon contact with water. Osmopolymers may be of plant or animal origin, or synthetic, and examples of osmopolymers are known in the art. Examples include: poly(hydroxy-alkyl methacrylates) with a molecular weight of 30,000 to 5,000,000; poly(vinylpyrrolidone) with a molecular weight of 3,000 to 20,000; anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000; a mixture of methyl cellulose, cross-linked agar and carboxymethylcellulose; a mixture of hydroxypropylmethylcellulose and sodium carboxymethylcellulose; polymers of N-vinyllactams, polyoxyethylene-polyoxypropylene gels; polyoxybutylene-polyethylene block copolymer gels; carob gum; polyacrylic gels; polyester gels; polyurea gels; polyether gels; polyamide gels; polypeptide gels; polyamino acid gels; polycellulosic gels; carbopol acidic carboxy polymers having molecular weights of 250,000 to 4,000,000; CYANAMER® polyacrylamides, cross-linked indene-maleic anhydride polymers; GOOD-RITE® polyacrylic acids having molecular weights of 80,000 to 200,000; POLYOX® Polyethylene oxide polymers having molecular weights of 100,000 to 5,000,000; starch graft copolymers; and Aqua-Keeps acrylate polymer polysaccharides.

The choice of a specific osmotic agent can be made based on the push power or push rate required of the engine. The osmotic agents especially useful in the present invention include carboxymethylcellulose and sodium, magnesium, zinc, and calcium salts. The salts include, but are not limited to, chloride, lactate, and sulfate. For example, salts useful in the present invention include, but are not limited to, sodium chloride (NaCl), magnesium chloride, zinc chloride, calcium chloride, sodium lactate, magnesium lactate, zinc lactate, calcium lactate, sodium sulfate, magnesium sulfate, zinc sulfate, and calcium sulfate. Preferably, the osmotic agent is sodium chloride.

An "osmotic engine" is the portion of an osmotic system comprising the osmotic agent composition and is capable of expanding upon imbibition of water.

A "beneficial agent" is any substance that can be used for a predetermined purpose, particularly a physiologically, pharmacologically or environmentally active substance. For example, the beneficial agent may be any agent that is known to be delivered to the body of a living organism, particularly a human or an animal, such as medicaments, vitamins, and nutrients. The terms "beneficial agent" and "drug" are used interchangeably herein.

A "viscous" composition is a composition having a viscosity of at least about 10 poise at shear rates of about 0.05 to about 5 per second. The viscosity of the composition is preferably at least about 50 poise, more preferably at least about 100 poise, and most preferably at least about 250 poise at shear rates of about 0.05 to about 5 per second.

A "shear rate" or "shear strain rate" is the rate of change of strain as a function of time. This strain occurs when a force is applied to a material and the material deforms under the force (or applied stress). The material's resistance to flow is its viscosity.

A "flowable" composition is a composition that is capable of changing shape autonomously when placed in containers with different shapes. For example, a flowable composition may be a liquid, solution, suspension, slurry or paste.

A "fluid vehicle" is a fluid used in the present invention which, when combined with the osmotic agent, results in a flowable composition. The vehicle should be capable of uniformly suspending the osmotic agent. The viscosity of the vehicle is dependent upon the engine push power needed to deliver the beneficial agent composition as well as on the viscosity necessary to prevent piston bypass or leakage.

A "homogeneous" osmotic composition is a composition in which the osmotic agent is distributed evenly.

"Limited osmotic power" refers to an osmotic power lower than the osmotic power of a saturated sodium chloride solution at 37° C. Saturated sodium chloride has an osmotic pressure value of 13 Os/kg.

"Infiltration activity" is the ability of a substance to enter the pores or interstices of a material. Infiltration activity is measured by measuring the weight change of the material over time with substance present, but without added water present.

A "zero order release rate" or "steady-state release rate" refers to a beneficial agent release rate that does not significantly vary with time. Typically, when an osmotic delivery system is first placed into a fluid environment of use, it begins to release the beneficial agent at a rate that changes significantly with time. After a period of time (the "startup time"), however, the release rate stabilizes and no longer varies significantly. The stable release rate at this point is the zero order release rate.

The Osmotic Delivery System

The present invention relates to an osmotic drug delivery system for delivering a beneficial agent. The delivery system according to the present invention comprises an osmotic engine in which the osmotic agent is contained in a viscous, flowable composition. The osmotic engine according to the present invention has a shortened startup time and rapidly reaches zero order push power or push rate. The delivery system according to the present invention has shortened startup time and rapidly reaches zero order release rate. Thus, the osmotic drug delivery system of the present invention works to provide delivery performance that is more predictable than prior osmotic systems.

FIG. 1 illustrates an example of an osmotic drug delivery system 10 according to the present invention. The configuration illustrated in FIG. 1 is one example of a drug delivery system and is not to be construed as limiting the present invention. The present invention is generally applicable to external and internal osmotic delivery systems having any number of shapes, and to all such systems administered in any methods such as oral, ruminal, and implantable osmotic delivery techniques.

The osmotic drug delivery system 10, as illustrated in FIG. 1, includes an elongated capsule 12 having a first open end 14 and a second enclosed end 16. The enclosed end 16 has one or more fluid delivery orifices 18. The elongated capsule 12 is made of a material that is sufficiently rigid to withstand expansion of an osmotic agent without changing size or shape. The elongated capsule 12 is also largely impermeable to fluids in the environment of use as well as to ingredients contained within the delivery system such that the migration of such materials into or out of the system through the impermeable material is so low as to have substantially no adverse impact on the function of the osmotic delivery system. Materials suitable for the capsule are known in the art and are discussed in, for example, U.S. Pat. No. 5,985,305, which is incorporated by reference herein in its entirety.

Within the capsule 12 is a first chamber 20 for containing a beneficial agent to be delivered. Such a beneficial agent may optionally include other beneficial agents, pharmaceutically acceptable carriers and/or additional ingredients such as antioxidants or stabilizing agents. The first chamber 20 is connected to the fluid delivery orifice(s) 18.

The embodiment of the present invention illustrated in FIG. 1 includes a movable partition or piston 22. A second chamber 24 within the capsule 12 is separated from the first chamber 20 by the movable piston 22. The second chamber 24 contains an osmotic engine 26, which is a viscous, flowable composition comprising at least one osmotic agent.

The movable piston 22 is a substantially cylindrical member that is configured to fit within the capsule 12 in a sealed manner that allows the piston to slide along a longitudinal direction within the capsule. The piston 22 may be in the form of a movable partition or a stationary and stretchable partition member. The piston 22 preferably is formed of an impermeable resilient material and includes annular ring shape protrusions (not shown) that form a seal with the inner surface of the capsule.

However, the present invention need not include the movable piston or partition 22; in such an embodiment, the first chamber 20 and the second chamber 24 are separated by an interface between the osmotic engine and the beneficial agent. Thus, when the osmotic delivery system is in use, the volumes of the first chamber 20 and the second chamber 24 change as the osmotic agent imbibes fluid from the surrounding environment, the volume of the second chamber 24 expands due to the imbibed fluid, and the volume of the first chamber 20 shrinks because a portion of the beneficial agent is released through the fluid delivery orifice(s).

As illustrated in FIG. 1, the drug delivery system 10 of one embodiment of the present invention includes a membrane plug 28 that is inserted in the first open end 14 of the capsule 12 after placing the osmotic engine 26 within the capsule. The membrane plug 28 is formed of a semipermeable material that allows fluid to pass from an exterior fluid environment into the second chamber 24 to cause the osmotic engine 26 to swell. However, the semipermeable material forming the membrane plug 28 is largely impermeable to the materials within the capsule and other ingredients within the fluid environment of use. Materials suitable for the semipermeable plug are known in the art and are discussed in, for example, U.S. Pat. No. 5,985,305, which is incorporated by reference herein in its entirety.

The Osmotic Engine

The osmotic engine in the present invention is a viscous, flowable composition that comprises at least one osmotic agent. Due to the osmotic agent, the osmotic engine is capable of expanding upon imbibition of water when placed in a fluid environment, thereby forcing the beneficial agent to pass through the opening of the compartment (delivery orifice) into the outside environment. The osmotic agent must be suspended, not dissolved in the viscous vehicle. Osmotic agent dissolved in the viscous vehicle will not produce the same total engine performance throughout the total release time period. The osmotic agent expands upon the absorption of liquid. If the osmotic agent is dissolved as a liquid in the engine composition, the osmotic agent has already expanded.

By using a flowable composition as the osmotic engine, the potential disadvantages of osmotic engines including a tableted osmotic composition can be reduced or eliminated. Currently, the engine of a drug delivery system such as that shown in FIG. 1 is made by inserting sodium chloride tablets into a compartment, then filling the remaining space with a filler, such as PEG 400. Alternatively, the filler is loaded into the compartment before the sodium chloride tablets are added. In either case, this involves a two-step assembly. Air can be entrapped in the salt tablets during manufacture. Moreover, because the sodium chloride tablets are a dry solid mass, air can be entrapped in the engine as the dry tablets are put into the engine. Since air is compressible, the engine begins to swell immediately upon imbibition of water but does not begin to push the piston until the air is compressed, potentially resulting in an undesirably long delay in startup. The entrapped air included in systems that utilize a tableted osmotic composition can also cause the performance of these systems to vary significantly from one system to another because the amount and/or distribution of air in each system may vary.

In the present invention, the osmotic agent is suspended in a fluid vehicle to form a viscous, flowable osmotic engine composition that is capable of imbibing water in a fluid environment. Therefore, a large quantity of this osmotic engine composition may be prepared for use in the manufacture of many systems, and the composition can be easily loaded into the engine compartment of the systems in a one-step process. Furthermore, the flowable osmotic engine composition entraps less or no air relative to tableted compositions, and the flowable osmotic engine composition of the present invention can be de-aerated before being loaded into an osmotic delivery system, which can further reduce the amount of air entrapped in the osmotic engine. As a result, the osmotic engine according to the present invention reduces or eliminates the potential delays and variability associated with osmotic engines that utilize tableted osmotic compositions. The osmotic delivery systems of the present invention, therefore, typically exhibit shortened startup times and reduced intersystem variations in delivery performance.

Figure 2:
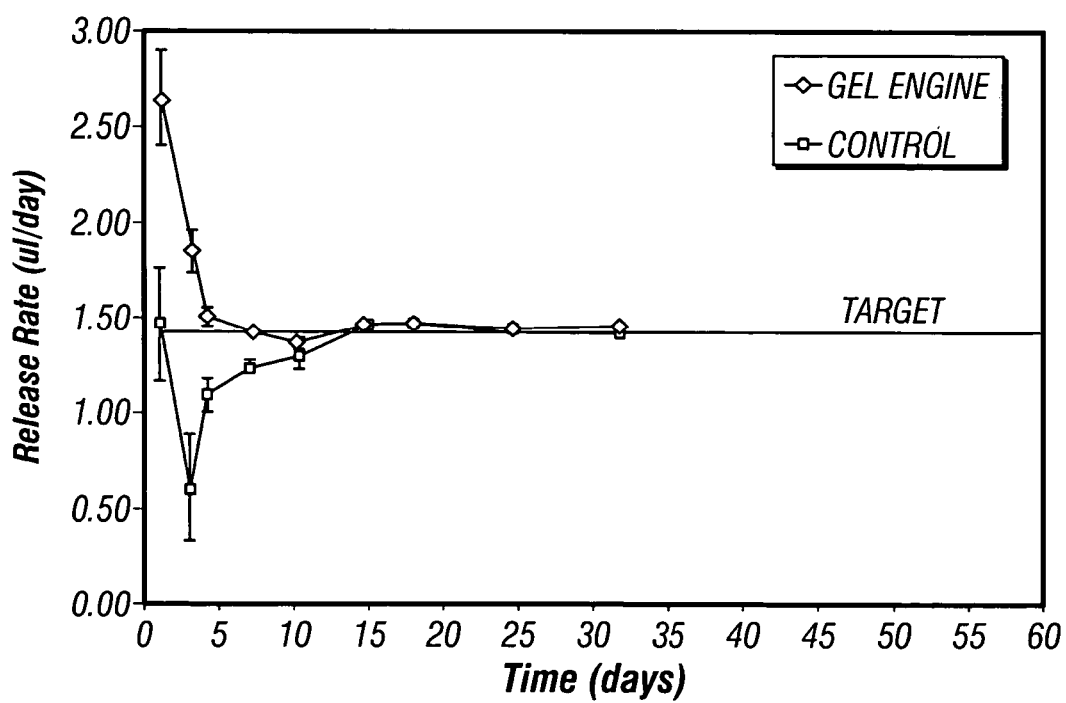
FIG. 2 shows a comparison of the performance of a flowable engine prepared according to one embodiment of the present invention and a control engine prepared by a conventional method. The flowable engine comprises a flowable, viscous vehicle prepared by mixing polyvinylpyrrolidone (PVF) and PEG 400 (polyethylene glycol). The PVP PEG 400 mixture is then mixed with sodium chloride. The control engine contains two sodium chloride tablets and PEG 400 as the filler. The release rate is also shown as a horizontal line labeled "target."

Example 1 illustrates the performance of a system containing a viscous, flowable osmotic engine composition according to the present invention as compared to a control system containing sodium chloride tablets as the engine. Although both the viscous flowable engine and the control engine contained similar components (mainly sodium chloride and PEG 400), the delivery profiles were very different. The delivery rate of the flowable osmotic engine stabilized much more quickly than the control engine (FIG. 2). Thus, the system with the flowable engine had a startup time of 4 days or less in a 30-day system, which is about 10% of the administration time. In contrast, the system with the control engine did not stabilize until 10 to 15 days into the 30-day life of the system. The systems according to the present invention preferably have a startup time of less than about 10% of the administration time of the system. More preferably, the startup time is less than about 7.5%, and most preferably less than about 5% of the total delivery duration. Shortened startup time can be achieved by careful selection of the fluid vehicle and osmotic agent.

Vehicles for this invention should have limited osmotic power. The amount of osmotic power exhibited by the vehicle will depend upon the amount of push power required to deliver the beneficial agent composition. If the delivery of beneficial agent requires a large amount of engine push power, a vehicle may be chosen with a higher limited osmotic power to increase the engine push power. If the delivery of beneficial agent requires a lower amount of engine push power, a vehicle may be chosen with a lower limited osmotic power so that the engine push power comes primarily from the osmotic agent.

While the fluid vehicle useful in the present invention may be any fluid compatible with the purpose of the system, the fluid vehicle preferably has limited osmotic power so that the osmotic power of the osmotic engine comes primarily from the osmotic agent, thereby rendering the performance of the system more predictable. Therefore, the fluid vehicle should have an osmotic power lower than that of a saturated solution of sodium chloride at 37° C.

Vehicles that can be used include, but are not limited to, polyethylene glycol (preferably with an average molecular weight of 100 to 600), polysorbates such as polysorbate 80 or TWEEN® 80, polyvinylpyrrolidone, vitamin E acetate, vegetable oils such as soybean oil, and glycerol. Preferred fluid vehicles for the flowable engine composition include, but are not limited to, polysorbates and vegetable oils. A preferred polysorbate is polysorbate 80. A preferred vegetable oil is soybean oil. It is also preferable to use a fluid vehicle that does not infiltrate the semipermeable membrane. If the fluid vehicle is capable of infiltrating the membrane, it may cause the membrane to swell and alter the permeability of the membrane. For example, a fluid vehicle that infiltrates the membrane may decrease the rate at which water can pass through the membrane, thereby decreasing the delivery rate of the osmotic system.

Example 2 demonstrates the effects of infiltration activity of the fluid vehicle on the semipermeable membrane. Groups of semipermeable membranes were floated in each fluid vehicle. Over time the membranes were removed from the vehicle and weighed to determine weight gain of the membranes. The system with soybean oil as the fluid vehicle achieved steady-state performance within the shortest period of time. The system with polysorbate 80 as the fluid vehicle delivered at a steady rate within 4 to 5 days in a 90-day engine, which is about 5% of the administration time.

For zero order engine push power and zero order beneficial agent delivery, the amount of fluid imbibed into the engine compartment through the semipermeable membrane must remain approximately constant. Thus, preferably, the flowable engine composition does not infiltrate or has low ability to infiltrate the semipermeable membrane so as not to alter the water permeability of the membrane.

It is also preferable to use a fluid vehicle that is capable of suspending a large amount of the osmotic agent. If a small volume of the fluid vehicle can accommodate a large amount of the osmotic agent, the size of the osmotic engine can be reduced, thereby reducing the size of the osmotic system or increasing the amount of beneficial agent the system can deliver.

In addition, the fluid vehicle should not be toxic to the recipient of the osmotic system if the system is to be used in a living organism or in contact with cultured cells. Although, under normal circumstances, the fluid vehicle is not permeable through the semipermeable membrane and has no other contact with the outside environment, toxicity of the vehicle should still be a concern in case of system breakage. On the other hand, the toxicity of the fluid vehicle is less important if the fluid vehicle is to be used in an osmotic system that is not used in a living organism or in contact with cultured cells. For example, the toxicity of the fluid vehicle may not affect the selection of a fluid vehicle that is used in an osmotic engine included in an external osmotic pump designed to be used in conjunction with a catheter, an intravenous line or any other device or system providing the delivery of a beneficial agent within a living organism or to cultured cells from a location that is external to the living organism or remote from the cultured cells.

The osmotic engine composition is preferably viscous so that the suspended particles of osmotic agent do not settle out. If the osmotic agent settles prior to or during packing of the engine composition into the system, the amount of osmotic agent in each system may vary. If the osmotic agent settles in an osmotic system during delivery of the beneficial agent, the release rate may vary due to the uneven distribution of osmotic agent in the engine. Therefore, the viscosity of the engine composition should be at least about 10 poise at shear rates of about 0.05 to about 5 per second. The engine composition preferably has a viscosity of at least about 50 poise, more preferably at least about 100 poise, and most preferably at least about 250 poise at shear rates of about 0.05 to about 5 per second. The viscosity required to maintain an osmotic agent in suspension will vary with the size and density of the osmotic agent particles, and can be determined empirically in each composition.

If the mixture of the osmotic agent and the fluid vehicle is not viscous enough, a thickening agent can be added to the engine composition. A thickening agent should possess the required viscosity, as well as limited osmotic power and low infiltration activity in the semipermeable membrane for the same reasons discussed above in relation to the fluid vehicle. An example of a thickening agent useful in the present invention is polyvinylpyrrolidone.

The osmotic engines of the present invention may further comprise a thickening agent to achieve the desired consistency or viscosity of the engine composition. The desired consistency or viscosity is dependent on the consistency needed to allow easy placement of the engine composition in the engine compartment of the osmotic delivery system, on the viscosity needed to reduce engine bypass or leakage, and on the amount of push power needed to deliver the beneficial agent composition. The thickening agent should preferably have limited or no osmotic power, as well as low or no infiltration activity in the semipermeable membrane.

Organisms to which beneficial agents may be administered using systems of this invention include humans and other animals. The invention is of particular interest for application to humans and household, sport, and farm animals, particularly mammals. For the administration of beneficial agents to animals, the systems of the present invention may be implanted subcutaneously or intraperitoneally where aqueous body fluids are available to activate the osmotic engine. Systems of the invention may also be administered to the rumen of ruminant animals, in which embodiment the systems may further comprise a density element for maintaining the system in the rumen for extended periods of time up to 120 days or longer. Density elements are well known in the art of drug delivery systems and are discussed in, for example, U.S. Pat. Nos. 4,874,388; 5,023,088; 5,938,654; and 5,997,902, which are incorporated by reference herein in their entireties.

The present invention applies to the administration of beneficial agents in general, which include any physiologically or pharmacologically active substance. The beneficial agent may be any agent or agents that are known to be delivered to the body of a human or an animal such as medicaments, vitamins, or nutrients.

Beneficial agents which may be delivered by the present invention include drugs which act on the peripheral nerves, adrenergic receptors, cholinergic receptors, skeletal muscles, the cardiovascular system, smooth muscles, the blood circulatory system, synoptic sites, neuroeffector junctional sites, endocrine and hormone systems, the immunological system, the reproductive system, the skeletal system, the autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by systems according to this invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phemnetrazine hydrochloride, bethanechol chloride, methhacholine chloride, pilocarpine hydrochloride, atropine sulfate, scopolamine bromide, isoproamide iodide, tridihexethyl chloride phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorphate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethoasone and its derivatives such as betamethasone, triamcinlone, methyltestosterone, 17-β-estradiol, ethinyl estradiol, ethinyl estradiol 3-methyl ether, prenisolone, 17-β-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, nilrinone, capropril, mandol, quanabenz, hydrochlorothiazide, ranitidine, flurbiprofen, fenufen, flurprofen, tolmetin, alclofenac, mefenamic, flufenamic acid, diflunisal, nimodipine, nitrendipine, nisoldipine, nicardipine, felodipine, lidoflazine, tiapamil, gallopamil, amlodipine, mioflazine, lisinopril, enalipril, enalaprilat, captopril, ramipril, famotidine, mizatidine, sucralfate, etintidine, tetratolol, mioxidil, chlordiazepoxide, diazepam, amitriptyline, and imipramine. Further examples are proteins and peptides which include, but are not limited to, insulin, colchicines, glucagons, thyroid stimulating hormone, parathyroid and pituitary hormones, calcitonin, rennin, prolactin, corticotrophin, thyrotropic hormone, follicle stimulating hormone, chorionic gonadoptropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons (including, but not limited to alpha, beta, gamma, omega), interleukins, growth hormones such as human growth hormone and porcine growth hormone, fertility inhibitors such as the prostaglandins, fertility promoters, growth factors, EGF, PDGF, coagulating factors, human pancreas hormone releasing factor, analogs and derivatives of these compounds, and pharmaceutically acceptable salts of these compounds, or their analogs or derivatives.

The beneficial agent can be present in this invention in a wide variety of chemical and physical forms, such as solids, liquids and slurries. On the molecular level, the various forms may include uncharged molecules, molecular complexes, and pharmaceutically acceptable salts such as hydrochlorides, hydrobromides, sulfate, laurylate, oleate, and salicylate. For acidic compounds, salts of metals, amines or organic cations may be used. Derivatives such as esters, ethers and amides can also be used. An active agent can be used alone or mixed with other active agents.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
min=minute
μM=micromolar
mM=millimolar
M=molar
ml=milliliter
μl=microliter
mg=milligram
μg=microgram
rpm=revolutions per minute
SDS=sodium dodecyl sulfate
PBS=phosphate buffered saline DMEM=Dulbecco's modified Eagle's medium
EGF=epidermal growth factor
PDGF=platelet derived growth factor
LHRH=luteinizing hormone releasing hormone
PEG=polyethylene glycol
pvp=polyvinylpyrrolidone Example 1

A fluid vehicle of a polyvinylpyrrolidone (pvp, MW 12,000):polyethylene glycol 400 (PEG 400) formulation (40:60) was mixed with NaCl to manufacture a 60-day engine. 30% (w/w) of the fluid vehicle and 70% (w/w) of NaCl were blended together under vacuum until a homogeneous suspension was formed. The suspension was loaded into a syringe. To assemble an osmotic delivery system, a cylindrical titanium reservoir was loaded with a plunger-type piston that created two compartments: the osmotic engine compartment and the beneficial agent compartment. The suspension engine composition was inserted into the entire osmotic engine compartment using a syringe and a needle. The engine end of the reservoir was then capped with a semipermeable membrane. The control system contained two NaCl tablets and a PEG 400 filler in the engine compartment. Blue dye was used in the place of the beneficial agent to assess the release rate.

To test the performance of the system, the osmotic system was placed in water, and the amount of blue dye released from the system was determined periodically. The blue dye release profile is shown in FIG. 2. After a short initial period in which the blue dye was delivered above the target level, the system with a flowable engine reached a steady rate of delivery after 4 to 5 days. In contrast, the control system did not stabilize until after about 15 days, and the delivery rate within those 15 days was below the target.

Figure 3:
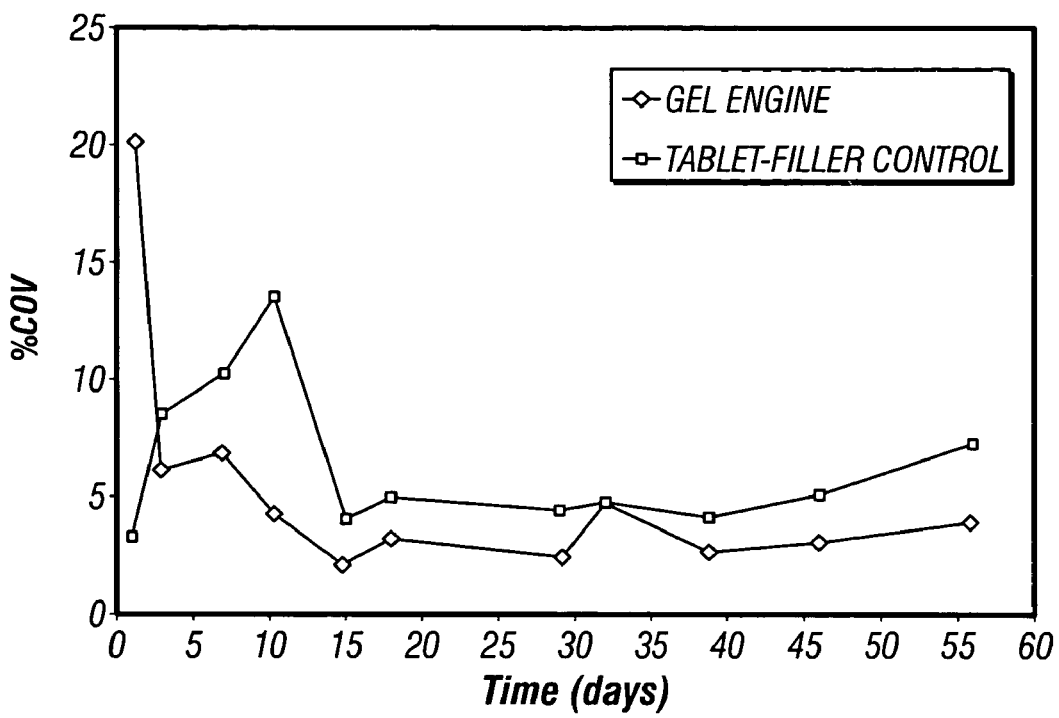
FIG. 3 shows a comparison of the percent coefficients of variation of the two engines described in FIG. 2.

FIG. 3 shows the percent coefficients of variation of the control and flowable engines. An engine subassembly, without the beneficial agent, was prepared for the flowable engine and the control engine, respectively. The subassemblies were then placed in water and the weight gain of each subassembly was measured periodically. From the 5 subassemblies tested for each type of engine, the average weight gain and the standard deviation were calculated. Percent coefficient of variation is the value of standard deviation divided by the average and is shown in FIG. 3. The variation of the flowable engine was much less than the control engine and stabilized quickly after the onset of imbibition.

Example 2

Fluid vehicles with limited osmotic power and low infiltration activity in the semipermeable membrane were used to make flowable engines with sodium chloride. A fluid vehicle with limited osmotic power is beneficial because if the fluid vehicle has osmotic power, this additional osmotic power will complicate the osmotic power of the osmotic agent, and the performance of the osmotic system may deviate from the predicted one. Similarly, a fluid vehicle that infiltrates the semipermeable membrane will cause the membrane to swell and may alter the imbibition rate by increasing or decreasing the rate at which water passes through the membrane. As a result, varying delivery rates are observed for an extended period of time before stabilization.

Table 1 shows the weight gain of membranes over time at 37° C. using soybean oil, glycerol, polysorbate 60, vitamin E acetate, or PEG 300 as a fluid vehicle in a flowable engine according to the present application. The control engine contained osmotic tablets and a PEG 400 filler. A group of semipermeable membranes (5–10) were floated in each vehicle. The membranes were removed from the vehicle and weighed at each time point. Table 1 below shows the average weight gain over the number of membranes tested in each vehicle. Soybean oil has low osmotic power and low infiltration activity in the semipermeable membrane. Polysorbate 60 is highly infiltrating in the membrane and has a low osmotic power. Vitamin E acetate has low osmotic power and low infiltration activity in the semipermeable membrane. PEG 300 has both high infiltration activity in the membrane and high osmotic power. As shown in Table 1, the system with the soybean oil-containing engine achieved steady-state performance within the shortest period of time. The control system took significantly longer to reach steady-state performance.

TABLE 1

Membrane Weight Gain over Time at 37° C.

| Vehicle | 0 Days | 3 Days | 7 Days | 14 Days | 20 Days | 28 Days | 38 Days | 45 Days |
|---|---|---|---|---|---|---|---|---|
| Glycerol | 0 | 0.44 | 0.94 | 1.38 | 1.89 | 2.52 | 2.37 | 2.391 |
| PEG300 | 0 | 8.21 | 12.06 | 14.71 | 17.23 | 18.31 | 17.95 | 18.18 |
| Soybean oil | 0 | 0.13 | 0.63 | 0.88 | 0.76 | 1.07 | | |
| Component control | 0 | −0.25 | −0.13 | −0.13 | −0.32 | −0.38 | −0.34 | −0.253 |

| Vehicle | 0 Days | 8 Days | 20 Days | 27 Days | 45 Days |
|---|---|---|---|---|---|
| Dry control | 0 | −0.26 | 0.13 | −0.07 | |
| Polysorbate 60 | 0 | 9.91 | 13.67 | 12.37 | |

| Vehicle | 0 Days | 1 Day | 4 Days | 6 Days | 11 Days |
|---|---|---|---|---|---|
| Vitamin E acetate | 0 | 2.26 | 3.19 | 3.49 | 3.60 |

Figure 4:
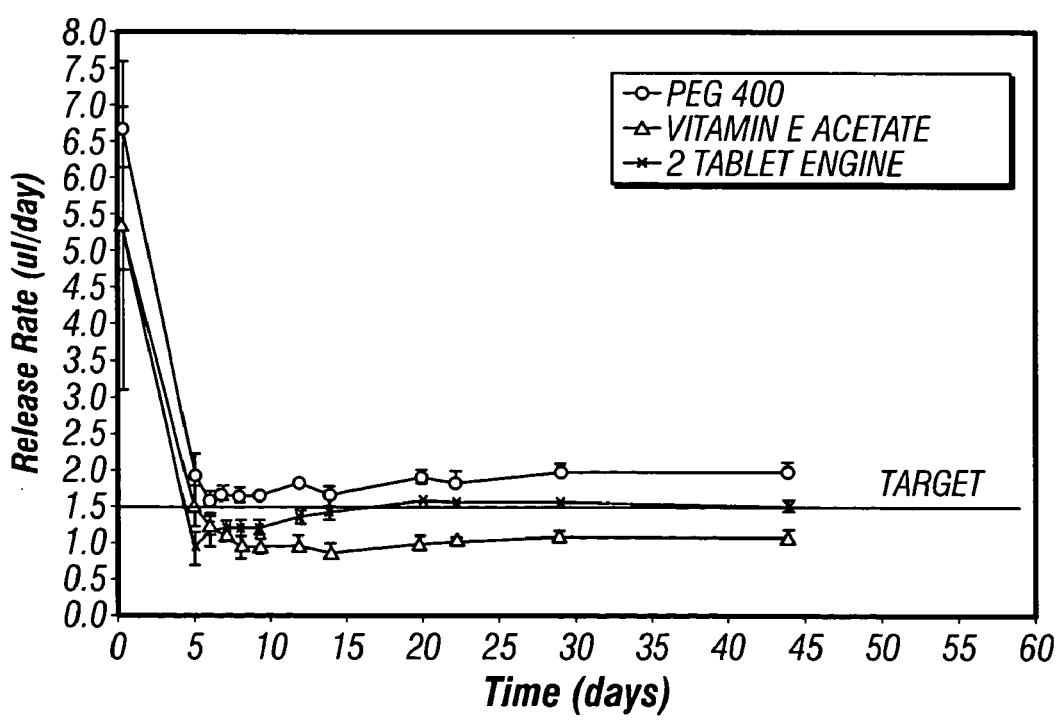
FIG. 4 shows the release profile of an implantable osmotic system containing a control engine, a flowable engine with PEG, or a flowable engine with vitamin E acetate, respectively, as the viscous vehicle. The number of systems tested (n) for each type of engine is also shown.
Figure 5:
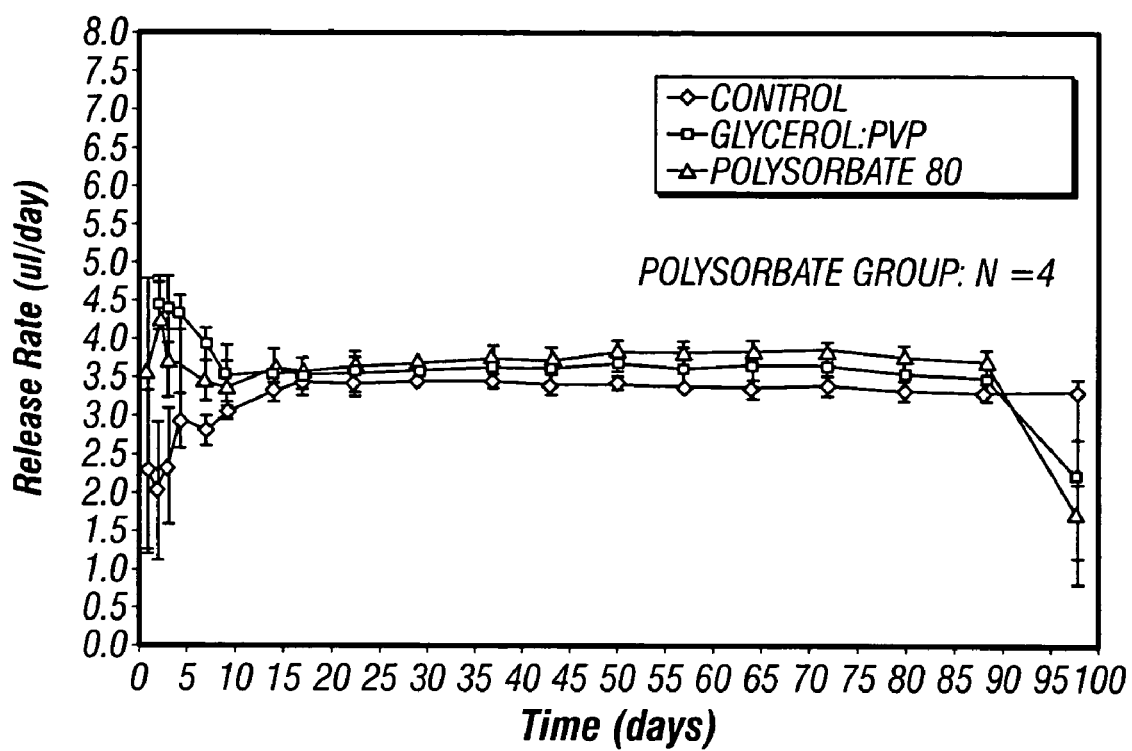
FIG. 5 shows the release profile of an implantable osmotic system containing a control engine, a flowable engine with glycerol and polyvinylpyrrolidone, or a flowable engine with polysorbate 80, respectively, as the viscous vehicle. The number of systems tested (n) for the engine with polysorbate 80 was four. The number of systems tested (n) for the engine with glycerol and polyvinylpyrrolidone was five.

FIGS. 4 and 5 indicate the average blue dye release rate from systems with sodium chloride suspended in PEG 400; vitamin E acetate; glycerol/polyvinylpyrrolidone; or polysorbate 80. The osmotic delivery systems were prepared in a manner similar to that described in Example 1 above. In both figures, the control system contained an engine with two sodium chloride tablets and PEG 400 as engine filler. Polysorbate 80 (which exhibits low osmotic power and low infiltration activity in the semipermeable membrane) exhibited the earliest steady-state performance and stabilized after 4 days in a 90-day engine.

Example 3

To determine if the present invention is applicable to delivery systems of various delivery durations, systems with a 45-, 90-, or 180-day delivery duration were tested and the results are summarized in Table 2. The flowable engine contained sodium chloride and polysorbate 80 prepared according to the present invention, whereas the control engine contained two sodium chloride tablets and the PEG 400 filler.

TABLE 2

Percent Startup to Total Delivery Duration

| | Delivery Duration (days) | Startup Time (days) | % Startup to Delivery Duration |
|---|---|---|---|
| Flowable engine | 45 | 3 | 6.7 |
| | 90 | 4 | 4.4 |
| | 180 | 8 | 4.4 |
| Control Engine | 90 | 12 | 13.3 |

These results show that the flowable engine significantly reduced the startup time of systems of every duration tested, and the effect is more profound when the delivery duration is longer.

This invention has been described in detail with particular reference to certain preferred embodiments thereof, but it will be understood that variations and modifications can be effected within the spirit and scope of the invention.

We claim:

1. An osmotic engine useful in an osmotic device for delivering a beneficial agent formulation, comprising:
   a flowable composition that increases in size upon imbibing fluid from a fluid environment through a semipermeable membrane in the osmotic device, the flowable composition comprising a viscous, fluid suspension vehicle with limited osmotic power and at least one particulate osmotic agent suspended in the viscous, fluid suspension vehicle.

2. The osmotic engine of claim 1 wherein the vehicle has low infiltration activity in the semipermeable membrane.

3. The osmotic engine of claim 1, wherein the vehicle is polysorbate or soybean oil.

4. The osmotic engine of claim 1, wherein the at least one osmotic agent is sodium chloride.

5. The osmotic engine of claim 1, further comprising a thickening agent.

6. The osmotic engine of claim 5, wherein the thickening agent is a polymer.

7. The osmotic engine of claim 6, wherein the polymer is present as 1 to 2% W/W.

8. An osmotic device for delivering a beneficial agent formulation, comprising:
   (a) a wall comprising in part a semipermeable membrane that allows fluid to pass through the membrane from a fluid environment;
   (b) a reservoir to store the beneficial agent formulation, the reservoir being inside the wall and having a passageway connecting the fluid environment with an interior of the reservoir; and
   (c) a viscous osmotic engine inside the wall and in contact with the semipermeable membrane, the engine being a flowable composition of at least one particulate osmotic agent suspended in a fluid suspension vehicle that has limited osmotic power;
   wherein the engine increases in size upon imbibing fluid from the fluid environment through the semipermeable membrane, and the increase in size creates a pressure on the reservoir containing the beneficial agent formulation so as to force the beneficial agent formulation to pass through the passageway outward to the fluid environment.

9. The osmotic device of claim 8, wherein the vehicle has low infiltration activity in the semipermeable membrane.

10. The osmotic device of claim 8, wherein the vehicle is polysorbate or soybean oil.

11. The osmotic device of claim 8, wherein the at least one osmotic agent is sodium chloride.

12. The osmotic device of claim 8, wherein the viscous osmotic engine further comprises a thickening agent.

13. The osmotic device of claim 12, wherein the thickening agent is a polymer.

14. A method for delivering a beneficial agent formulation into a fluid environment of use, comprising:
   (a) placing in the fluid environment an osmotic device, the osmotic device comprising:
      (1) a wall comprising at least in part a semipermeable membrane that allows water to pass through the membrane from the fluid environment;
      (2) a reservoir to store the beneficial agent formulation, the reservoir being inside the wall and having a passageway connecting the fluid environment with an interior of the reservoir; and
      (3) an osmotic engine, the engine being a flowable composition prepared by mixing at least one particulate osmotic agent and a fluid suspension vehicle with limited osmotic power to form a viscous flowable compositon and packed into a compartment inside the wall; and
   (b) allowing the osomotic engine to imbibe from the fluid environment through the semipermeable membrane and create a pressure on the reservoir containing the beneficial agent formulation so as to force the beneficial agent formulation to pass through the passageway outward to the fluid environment.

15. The method of claim 14, wherein the vehicle has low infiltration activity in the semipermeable membrane.

16. The method of claim 14, wherein the vehicle is polysorbate or soybean oil.

17. The method of claim 14, wherein the at least one osmotic agent is sodium chloride.

18. The methof of claim 14, wherein the engine further comprises a thickening agent.

19. The method of claim 18, wherein the thickening agent is a polymer.

* * * * *

UNITED STATES PATENT AND TRADEMARK OFFICE
CERTIFICATE OF CORRECTION

PATENT NO. : 7,074,423 B2
APPLICATION NO. : 10/463300
DATED : July 11, 2006
INVENTOR(S) : Pamela J. Fereira et al.

Page 1 of 1

It is certified that error appears in the above-identified patent and that said Letters Patent is hereby corrected as shown below:

Column 16, line 35, claim 14: Delete "compositon", insert --composition--

Column 16, line 37, claim 14: Delete "osomotic", insert --osmotic--

Column 16, line 50, claim 18: Delete "methof", insert --method--

Signed and Sealed this
Sixteenth Day of August, 2011

David J. Kappos
*Director of the United States Patent and Trademark Office*